(12) United States Patent
Flores et al.

(10) Patent No.: US 7,824,122 B2
(45) Date of Patent: Nov. 2, 2010

(54) LIQUID APPLICATOR AND METHOD FOR REDUCING THE CONCENTRATION OF BY-PRODUCTS FROM ANTISEPTIC

(75) Inventors: Jesus Flores, El Paso, TX (US); Scott A. Tufts, Leawood, KS (US); Angel G. Magallon, El Paso, TX (US); James R. Bardwell, El Paso, TX (US)

(73) Assignee: Carefusion 2200, Inc., San Diego, CA (US)

( * ) Notice: Subject to any disclaimer, the term of this patent is extended or adjusted under 35 U.S.C. 154(b) by 850 days.

(21) Appl. No.: 11/674,899

(22) Filed: Feb. 14, 2007

(65) Prior Publication Data

US 2007/0231051 A1    Oct. 4, 2007

Related U.S. Application Data

(60) Provisional application No. 60/773,261, filed on Feb. 14, 2006.

(51) Int. Cl.
*B43K 5/14* (2006.01)
*A61K 7/50* (2006.01)

(52) U.S. Cl. .................. 401/134; 401/133; 401/196; 604/3; 510/130

(58) Field of Classification Search .............. 401/133, 401/134, 196; 604/3; 510/130
See application file for complete search history.

(56) References Cited

U.S. PATENT DOCUMENTS

| 5,690,958 | A | 11/1997 | McGrath |
| 7,614,812 | B2 * | 11/2009 | Reddy et al. ............... 401/133 |
| 2002/0041899 | A1 | 4/2002 | Chudzik et al. |
| 2003/0138492 | A1 | 7/2003 | Rozzi et al. |
| 2004/0179888 | A1 | 9/2004 | Tufts et al. |
| 2005/0119313 | A1 | 6/2005 | Behrends et al. |

FOREIGN PATENT DOCUMENTS

JP    2005289959 A    10/2005

* cited by examiner

*Primary Examiner*—David J Walczak
(74) *Attorney, Agent, or Firm*—Arent Fox LLP

(57) ABSTRACT

Applicators and a method for reducing the concentration of unwanted chemicals, such as para-chloroaniline (PCA) from an antiseptic solution. More specifically, the applicator includes antiseptic solution in amount sufficient to be applied to a desired surface and to have an antimicrobial effect on the desired surface and a porous element. The porous element selectively removes undesired by-products from the antiseptic solution when the antiseptic solution contacts the at least one porous element.

20 Claims, 2 Drawing Sheets

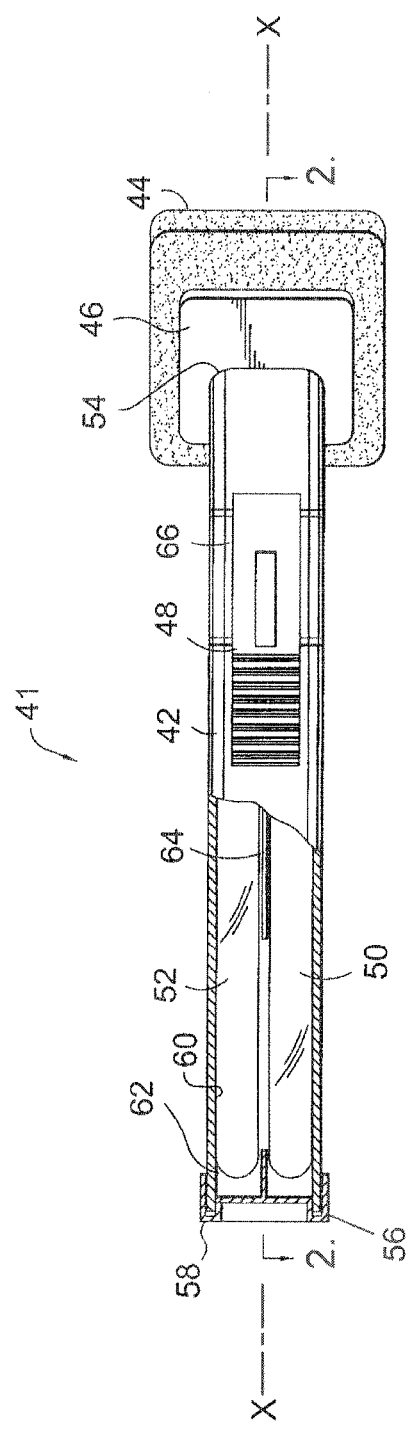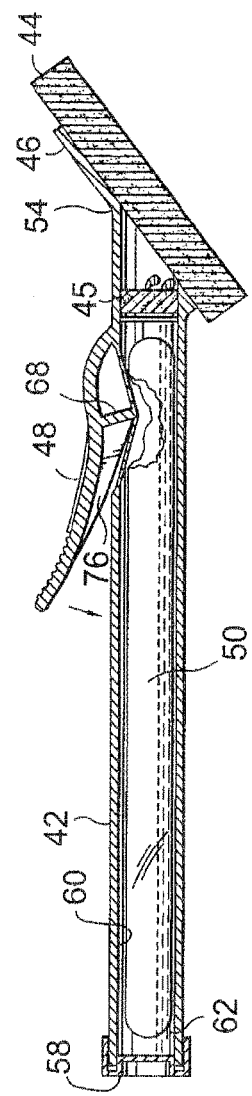

_US 7,824,122 B2_

LIQUID APPLICATOR AND METHOD FOR REDUCING THE CONCENTRATION OF BY-PRODUCTS FROM ANTISEPTIC

CROSS-REFERENCE TO RELATED APPLICATIONS

This application claims the benefit of priority of U.S. Provisional Application Ser. No. 60/773,261 filed on Feb. 14, 2006, the entirety of which is incorporated by reference.

STATEMENT REGARDING FEDERALLY SPONSORED RESEARCH OR DEVELOPMENT

Not Applicable.

BACKGROUND

Antisepsis is the destruction or inhibition of microorganisms that exist on living tissue. Antiseptics kill or prevent the growth of the microorganisms. Commonly used antiseptics include iodine, boric acid, and alcohol. Another antiseptic used is chlorhexidine gluconate (CHG). CHG exhibits a strong affinity for binding to skin, has a high level of antibacterial activity, and prolonged residual effects. It has been found that CHG is rapid acting, persistent and superior pre-operative skin preparation and kills more bacteria than traditional iodophors or alcohol. CHG exhibits rapid activity against gram-positive and gram-negative bacteria. However, as CHG decomposes, an unfavorable and potentially dangerous by-product of para-chloroaniline (PCA) is produced. Furthermore, as other antiseptics, such as alexidine, olanexidine, octenidine and quarternary amine compounds decompose, unwanted by-products are also produced.

SUMMARY

In one embodiment, an applicator for applying an antiseptic solution to a desired surface and for selectively removing undesired by-products from the antiseptic solution is provided. The applicator comprises an antiseptic solution in amount sufficient to be applied to a desired surface and to have an antimicrobial effect on the desired surface. The antiseptic solution comprises aqueous chlorhexidine gluconate. Aqueous chlorhexidine gluconate is a solution in which water is the solvent in the largest concentration by volume. The applicator further comprises at least one porous element, where the porous element selectively removes undesired by-products from the antiseptic solution when the antiseptic solution contacts the at least one porous element. In one embodiment, the undesired by-product is para-chloraniline and the least one porous element is a hydrophilic polyester-polyurethane foam material. The hydrophilic polyester-polyurethane foam material has pore sizes from 70 to 130 per linear inch and reduces the para-chloraniline in the antiseptic solution by 50-90%. The porous element may be a wetted applicator sponge or part of an applicator whereby the antiseptic solution is released from the at least one ampoule and flows through the at least one porous element.

In anther embodiment, an applicator for applying an antiseptic solution to a desired surface and for selectively removing undesired chemicals from the antiseptic solution is provided. In this embodiment, the applicator comprises antiseptic solution in amount sufficient to be applied to a desired surface and to have an antimicrobial effect on the desired surface. The antiseptic solution is selected from the group consisting of aqueous chlorhexidine, alexidine, octenidine, alexidine, olanexidine and salts thereof. The applicator also comprises at least one porous element, where the at least one porous element selectively removes undesired chemicals from the antiseptic solution when the antiseptic solution contacts the at least one porous element.

In yet another embodiment, a method for selectively removing unwanted by-products from an antiseptic solution is provided. An antiseptic solution in amount sufficient to be applied to a desired surface and to have an antimicrobial effect on the desired surface is provided. The antiseptic comprises aqueous chlorhexidine gluconate. The antiseptic solution is contacted with a porous element, wherein the porous element selectively removes para-chloraniline from the antiseptic solution.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means, instrumentalities and combinations particularly pointed out in the appended claims.

BRIEF DESCRIPTION OF THE DRAWINGS

FIG. 1 is a perspective view of a liquid applicator constructed in accordance with an embodiment of the invention; and FIG. 2 is a side plan view of a liquid applicator constructed in accordance with an embodiment of the invention;

DETAILED DESCRIPTION

Figure 3:
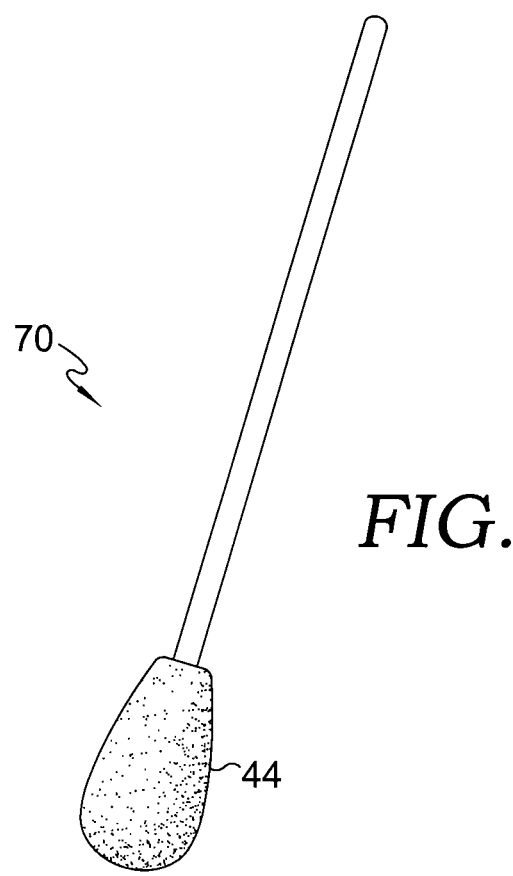
FIG. 3 is a perspective view of a liquid applicator swab in accordance with an embodiment of the present invention.

In one embodiment, a method for reducing the concentration of unwanted chemicals from antiseptic is provided. The antiseptic contacts a porous element, such as a hydrophilic ester polyurethane foam or felt, to reduce the concentration of unwanted chemicals, degradants, and by-products, such as para-chloraniline (PCA), in the antiseptic. The PCA, or other unwanted chemical, acts as a Lewis base and has a pair of lone electrons. The foam or felt material acts as a Lewis acid and accepts PCA, or other unwanted chemical impurities, as the antiseptic contacts the foam or felt material thus reducing the concentration of the unwanted chemical or by-product, such as PCA, in the antiseptic.

Antiseptics that may be employed to provide antimicrobial activity for compositions of the present invention include chlorhexidine, olanexidine, alexidine and octenidine and salts thereof. The chlorhexidine salt used in preferred embodiments is chlorhexidine gluconate (CHG). Although CHG is the chlorhexidine salt presented in the examples below, the present invention should not be limited to CHG as other types of chlorhexidine salts are suitable. Examples of such suitable chlorhexidine salts include gluconate, acetate, chloride, bromide, nitrate, sulphate, carbonate, and phosphanilate. The concentration of chlorhexidine or a chlorhexidine salt in the aqueous antiseptic solution may vary within various embodiments of the present invention. However, in some embodiments, the concentration of chlorhexidine or a chlorhexidine salt is about 0.1% w/v to about 10.0% w/v. Preferably, the aqueous antiseptic solution includes about 2.0-6.0% w/v CHG. The unwanted by-product of chlorhexidine gluconate is para-chloranaline.

An aqueous solution is any solution in which water is the primary dissolving medium or solvent. In other words, the term "aqueous solution" refers to a solution in which water is the solvent in the largest concentration by volume. As such, in an aqueous CHG solution, water is the solvent in the largest concentration by volume.

To prepare an aqueous CHG solution, 1 gram of PVP (average molecular weight 10,000) is dissolved in 30 ml of distilled water. Then, 5 ml of PEG (average molecular weight 200) is added. Additionally, 10.6 grams of 20% w/v aqueous CHG solution is provided and dissolved water is added until the 100-ml mark was reached. A small amount of alcohol may be added to the aqueous CHG solution. The aqueous CHG solution may be added to a glass ampoule, which was then sealed and placed inside the hollow body of the liquid applicator. Alternatively, the aqueous CHG solution may be poured over or sprayed onto a porous element and packaged as a wetted product such as a wetted swab or sponge.

Other antiseptics that may be utilized include: olanexidine, alexidine, octenidine and other quaternary amine compounds and salts thereof. For example, the antiseptics may include alexidine dihydrochloride, octenidine dihydrochloride, octenidine digluconate and octenidine mesylate, and olanexidine hydrochloride. Unwanted by-products and impurities of octenidine dihydrochloride may include 1-chloro-10(N-octyl-4-aminopyridinium)-decane-hydrochloride, N[1-[10-(4-amino-1(4H)-pyridinyl)-decyl]-4(1H)-pyridinylidene]-octanamine -dihydrochloride, acetone, N,N-dimethylformamide, 1,10 dichlordecane, and N-octyl-4-pyridinamine.

Antiseptic solutions in accordance with some embodiments of the present invention may employ additional components. For example, in some embodiments, the antiseptic solution may employ a surfactant. Examples of such suitable surfactants include polyvinyl pyrrolidone (PVP) (average molecular weight 10,000) and PVP (average molecular weight 1,300,000). In embodiments, the concentration of surfactant in an aqueous antiseptic solution may generally range from about 0.5% w/v to about 5% w/v. In a preferred embodiment, PVP (average molecular weight 10,000) in added as a surfactant in a concentration of about 1% w/v.

Additionally, in some embodiments, antiseptic solutions may employ a solubilization aid. Examples of such suitable solubilization aids include polyethylene glycol (PEG) (average molecular weight 200), PEG (average molecular weight 400), and glycerol. The concentration of a solubilization aid in an aqueous antiseptic solution of embodiments of the present invention may generally range from about 1% v/v to about 49% v/v. In a preferred embodiment, PEG (average molecular weight 200) is added as a solubilization aid in a concentration of about 1% v/v to about 49% v/v.

Colorants and dyes may also be included in the antiseptic solution. The colorants may include, but are not limited to, anionic FD&C dyes, such as, for example, FD&C Blue No. 1 (Brilliant Blue FCF), FD&C Blue No. 2 (Indigo Carmine), FD&C Green No. 3 (Fast Green FCF), FD&C Red No. 3 (Erythrosine), FD&C Red No. 40 (Allura Red), FD&C Yellow No. 5 (Tartrazine), and FD&C Yellow No. 6 (Sunset Yellow FCF) and cationic dyes such as crystal violet, acriflavine, bismarck brown, malachite green, methyl green, Victoria pure blue BO, and azure.

Additional additives may also be employed within antiseptic solutions of further embodiments of the present invention, including. Such additives would be employed in acceptable manners and amounts established in the art.

The porous element may be made of any porous material that allows liquid to flow through the material. The porous element may be hydrophobic or hydrophilic foam or a felt material, such as polyurethane foam or felt. In one embodiment, the porous element is a hydrophilic ester polyurethane foam utilized with aqueous CHG. The hydrophilic ester polyurethane foam has pore sizes preferably in the ranges of from 70 to 130 per linear inch, most preferably 70 to 90 pores per linear inch. The hydrophilic ester polyurethane foam may also have a double cell or sea sponge-like structure. The double cell structure has a distribution of larger and medium sized cells scattered across a background of finer cells. The larger cells may range from 0.06 to 0.09 inches in diameter.

The hydrophilic polyester polyurethane foam is made by reacting one or more polyols with one or more isocyanates in the presence of a catalyst as described in U.S. patent application Ser. No. 11/353,816, the entirety of which is hereby incorporated by reference. The hydrophilic ester foam material utilized with aqueous CHG includes: from at least about 30.0 parts by weight of an isocyanate; from 1.5 to 5.0 parts of a blowing agent, such as water; from 0.5 to 2.0 parts of a blow catalyst; from 0 to 0.3 parts of a gel catalyst, and up to 3.0 parts of a cell opening surfactant, such as a stabilizing silicone surfactant.

The hydrophilic ester polyurethane foam material utilized with aqueous CHG antiseptic has a density of about 1.70-2.40 LB/FT$^3$, a minimum tensile strength of about 10 PSI, a minimum elongation of about 300%, a minimum 25% CLD of 0.20 PSI, a minimum 65% CLD of 0.30 PSI, a minimum tear of 2.5 PLI and a maximum 50% compression set of 50%. The hydrophilic ester polyurethane foam material wets out in about five (5) seconds.

The more contact the antiseptic has with the internal surfaces of foam, the greater opportunity for the binding of unwanted chemicals, such as antiseptic by-products, to occur. The binding of the unwanted by-products to the foam material may be a function of pore size, pore volumes and internal surface of the applicator part exposed to the antiseptic. The shape of the porous element, such as a foam material, utilized with a liquid applicator may be any variety of shapes, including a disc, square of wedge. The preferred diameter of a disc is about 1.5 inches. The preferred size of the square is about 2.13 inches by 2.13 inches. The size of a wedge shaped foam is preferably has a length of about 2-4 inches and a width of 1.5-3 inches.

The porous element of the present invention also may take many forms. The porous element may be a porous plug and/or a porous pad. In other words, a porous plug may be located within the body of the applicator between the ampoule and an open end of the body. Additionally or alternatively, a porous pad may be located at an open end of the body.

In one embodiment, a liquid applicator for applying a desired antiseptic to a surface is provided. The liquid applicator further comprises at least one porous element capable of removing unwanted by-products, such as PCA, from antiseptic. When the antiseptic contacts the porous element, unwanted chemicals, such as PCA, are removed from the antiseptic. The filtered antiseptic may be applied to the desired surface.

The liquid applicator contains an amount of antiseptic solution of a sufficient amount to be applied to a desired surface and have an antimicrobial effect on the desired surface. In one embodiment, the desired surface is a patient's skin. It will be appreciated that the amount of antiseptic solution need to have an antimicrobial effect on a desired surface to which the antiseptic is applied may vary. In one embodiment the amount of antiseptic solution needed is 0.01-100 ml of antiseptic. More preferably, the amount of antiseptic solution need is about 0.5-60 ml of antiseptic. However, it will be appreciated that any amount that has an antimicrobial effect on a desired surface may be utilized with the liquid applicator and method.

It will be appreciated that the concentration of unwanted chemicals may be reduced by any amount. The level of unwanted chemicals may be reduced to below detection limits. With respect to aqueous CHG, the preferred amount of decrease in PCA may vary from 1-100%, preferably about 50-90%. At the same time, the decrease in the amount of antiseptic may be reduced by any amount. With respect to aqueous CHG, the preferred amount the CHG concentration is reduced may vary from 1-50%, preferably 1-15%, and most preferably 1-5%.

In one embodiment, the applicator comprises a hollow body defining an internal chamber to receive antiseptic to be applied. The porous element is positioned closing off the hollow body such that the antiseptic flows though the porous element. As the antiseptic flows through the porous element, unwanted chemicals, such as PCA, are removed from the antiseptic. In one embodiment, the antiseptic is contained in a frangible ampoule which is received by the internal chamber.

If the antiseptic is contained in an ampoule, it will be appreciated that the ampoule(s) may be numerous different shapes and sizes depending on the amount of liquid needed to be applied. For example, the applicator of the present invention may include long cylindrical ampoule(s) or may contain vial-type ampoule(s). Furthermore, more than one ampoule may be received by the body. Preferably, the ampoule(s) are formed of glass, although other materials are entirely within the scope of the present invention. The wall of the ampoules is of a thickness sufficient to contain the desired liquid during transport and storage, yet allow the ampoule to be fractured upon the application of localized pressure.

The body of the present embodiment of the invention may take many forms. If the antiseptic is contained in an ampoule, the body has an internal chamber that is adapted to receive at least one ampoule. The body may also be shaped to hold multiple ampoules. In one form, the body is shaped to generally conform to the ampoule(s) contained within the body.

The porous element of the present invention also may take many forms. The porous element may be a porous plug and/or a porous pad. In other words, a porous plug may be located within the body of the applicator between the antiseptic and an open end of the body. In an alternative embodiment, a porous pad may be located at an open end of the body or may be independent of a body. The porous element is positioned such the antiseptic flows through the porous element and at least some of the unwanted chemicals, such as PCA, are removed by the porous element from the antiseptic. The porous element may be made of any porous material that allows liquid to flow through the material. The porous element may be hydrophobic or hydrophilic foam or a felt material, such as polyurethane foam or felt.

If the antiseptic is contained in one or more ampoule(s), the ampoule(s) contained within the body of the applicator may be broken by any method known to those skilled in the art. These include, but are not limited to, squeezing the walls of the body inwardly to break the ampoule(s), using a lever or other mechanism to break the ampoule(s), or utilizing projecting wings with tappets as described below. If the antiseptic is not contained in one or more ampoule(s), the liquid may be forced from the body of the applicator in any variety of ways known to those skilled in the art.

Referring to FIG. 1 and FIG. 2, where like reference numerals identify like elements in the various views, a liquid applicator manifesting aspects of the invention is illustrated and designated generally by the numeral 41. Applicator 41 generally includes a body 42, and a porous pad 44 secured to flange 46 of body 42 and a lever 48. The exemplary liquid applicator 41 is meant to be illustrative rather than restrictive. It will be appreciated that the liquid applicator may take any various forms.

Two ampoules 50 and 52 are received in body 42. The liquid applicator 41 is constructed to house two 13 ml ampoules. It will be appreciated in other embodiments, that the liquid applicator may contain one ampoule, no ampoules or more than two ampoules. The thickness of the walls of the 13 ml ampoules is about 0.3 mm. However, ampoules of various sizes may be used. Ampoules 50 and 52 may be used for containing various liquids such as medicaments, cleansing agents, cosmetics, polishes or the like. In the illustrated embodiment, ampoules 50 and 52 contain antiseptic solution to be applied to a patient's skin prior to surgery. Ampoules 50 and 52 are illustrated as elongated cylinders with a central longitudinal axis. However, it will be appreciated that the principles of the present invention also may be applied to spherical or elongated polygonal ampoules. Furthermore, it will be appreciated that the principles of the present invention may be applied to more than two ampoules.

In one embodiment, ampoules 50 and 52 are formed of glass, although other materials are entirely within the scope of the present invention. In the illustrated embodiment, ampoules 50 and 52 are placed side by side within body 42. The wall of glass ampoules 50 and 52 is of a thickness sufficient to contain the desired liquid during transport and storage, yet allow ampoules 50 and 52 to be fractured upon the application of localized pressure.

Body 42 is generally hollow and oval or elliptical in shape and includes axially opposed first and second ends 54, 56. The proximal first end 54 is open and distal second end 56 is closed with cap 58. Illustrated body 42 is formed of high-density polyethylene, although any material exhibiting similar flexibility and integrity may be used. In the illustrated embodiment, body 42 and cap 58 were molded with 100% virgin material DOW, HDPE, Resin # 12454N, as defined in FDA Master File Number 4251. In the preferred embodiment, second end 56 is closed with cap 58, however second end may also be closed during the molding process obviating the need for a cap or the like.

Body 42 includes an interior wall 60 which defines an internal chamber 62 within body 42. Interior wall 60 is shaped to conform generally to the shape of ampoules 50 and 52 which are received within internal chamber 62. The circumference of interior wall 60 is slightly larger than the outer surface of the two ampoule bodies. Dividing wall 64 of hollow body 42 separates ampoules 50 and 52 and maintains ampoules 50 and 52 within internal chamber 62. Illustrated body 42 is elongated and defines a central longitudinal axis "x".

The thickness of the wall of the applicator may be between 0.040 to 0.080 inches and preferably is approximately 0.060 inches, except thin wall 66. The thickness of the wall of body 42 is reduced around crush area 66. Thin wall 64 may be between 0.020 to 0.040 inches and preferably is 0.030 inches. However, it will be appreciated that different wall sizes may be used within the scope of the embodiment of the invention. Thin wall 64 makes it easier for crush portion 68 of lever 48 to fracture multiple ampoules when lever 48 is depressed. This will be discussed in more detail later.

Body 42 further presents a flange 46 protruding from proximal end 54 along the periphery thereof. In the preferred embodiment, flange 46 is continuously molded to body 42 and is disposed at an angle. Preferably, flange 46 is disposed an angle of 45°, with respect to the central longitudinal axis of the body. It will be appreciated that flange 46 may be disposed at a variety of angles with respect to the central longitudinal axis of body 42. Flange 46 is adapted to support porous pad 44, as more fully described below.

Porous pad 44, such as foam or felt, closes off open end 54 of body 42. Porous pad 44 is received on flange 46 and encloses ampoules 50 and 52 within internal chamber 62. The porous pad 44 may be formed of felt or an open-celled foam material. In the illustrated embodiment, porous pad 44 is formed of hydrophilic polyester-polyurethane foam.

Porous pad 44 is cut from a sheet of foam or felt material having the desired porosity for the antiseptic to be dispensed. Porous pad 44 is preferably generally square in shape although it will be appreciated that the pad may be of any desired size and shape which is capable of being supported on flange 46.

In the illustrated embodiment, a woven or non-woven laminate material is laminated to porous pad 44. The material laminate material may be a woven or non-woven polyester material. The laminate material is positioned between porous pad 44 and flange 46 of body 42. As such, the laminate material functions to prevent shards of glass from the fractured ampoules from pushing through the porous pad during use of the applicator. The laminate material also provides a suitable welding material for securing the porous pad in place on the body when an ultrasonic welding operation is used to manufacture the applicator.

In one embodiment, a porous plug 45 may be positioned between porous pad 44 and ampoules 50 and 52. Porous plug 45 may be an open-celled foam material or felt. A porous plug can control the rate liquid flows from the body and prevent shards of glass from pushing through porous pad 44 during use of the applicator. A porous plug may be cut from a sheet of foam or felt material having the desired porosity for the liquid to be dispensed.

Body 42 also includes a lever 48 projecting from the top portion of body 42. However, it will be appreciated that lever 48 may project from any portion of body 42. Lever 48 is any mechanism for fracturing more than one ampoule at substantially the same time.

In use, applicator 41 presents a hand-held liquid applicator wherein lever 48 is depressed to release the desired liquid contained within ampoules 50 and 52 therein for application to a surface. Once lever 48 has been sufficiently depressed, the resulting forces fracture ampoules 50 and 52 almost simultaneously, thus releasing the liquid contained in each ampoule. The released liquid under the force of gravity flows down body 42, saturating porous pad 44. Consequently the liquid flows through porous pad 44 and at least some of the unwanted chemicals, such as PCA, are removed from the antiseptic. The filtered antiseptic flows through open end 54 and through porous pad 44. Thereafter, application of the filtered antiseptic is accomplished by bringing porous pad 44 into contact with the desired surface.

With reference to FIG. 3, a swab stick 70 having a porous element 44 is shown. The porous element 44 of swab stick 70 is wetted or saturated with an antiseptic, such as aqueous CHG. The swab may be placed into an impervious package, such as a sealed plastic or foil wrapper. As the antiseptic comes in contact with the porous element 44, unwanted chemicals, such as PCA, are removed by the porous element from the antiseptic. In the illustrated embodiment, the porous element is hydrophilic polyester-polyurethane foam.

Figure 4:
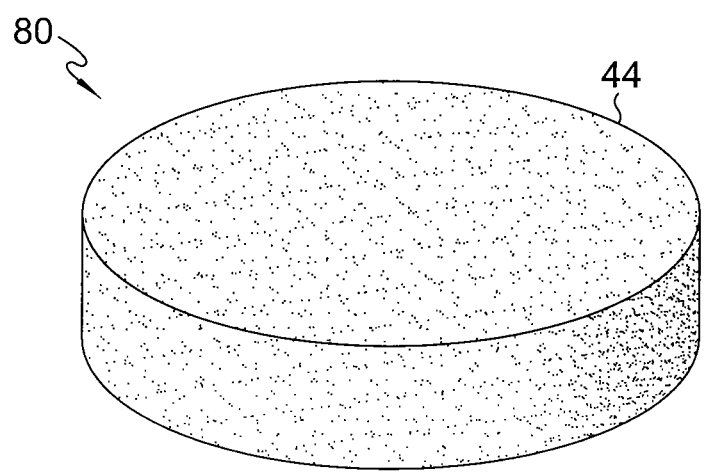
FIG. 4 is a perspective view of a wetted liquid applicator sponge in accordance with an embodiment of the present invention.

With reference to FIG. 4, a wetted sponge 80 having porous element 44 is shown. The porous element 44 is wetted or saturated with an antiseptic, such as aqueous CHG. The sponge 80 may be placed in an impervious package, such as a sealed plastic or foil wrapper. As the antiseptic contacts the porous element, unwanted chemicals, such as PCA, are removed by the porous element from the antiseptic. In the illustrated embodiment, the porous element is hydrophilic polyester-polyurethane foam.

EXAMPLE 1

Hydrophobic and hydrophilic polyurethane foams and felts for use as porous elements with embodiments of the present invention were tested to determine if the level of PCA was reduced when passed through the foam or felt material.

The porous elements for 26 ml applicators were die cut by E. N. Murray Co. from five variations of Libero hydrophilic polyester-polyurethane foam samples (labeled A, B, C, D and E) and 3-100Z felt material SIF-# 3-1000Z felt, (Natural Color Non-Pigmented) Reticulated Polyester Urethane obtained from Foamex International Inc. at 1000 Columbia Avenue Linwood, Pa. 19061. Two-26 milliliter applicators were assembled as described above using each of the Libero foams and 3-1000Z felt. The applicators were sent through a standard Ethylene Oxide (EtO) sterilization cycle.

One hundred (100) ppm of PCA was added to an aqueous 2% CHG solution. Twenty-six (26) ml the solution was added to six separate 26-ml applicators. Each applicator body was closed off by a different Libero foam (A-E) or the 3-1000z felt material. The PCA concentration of each solution before it passed through the foam or felt material was obtained. The CHG concentration of each solution in the applicators closed off by Libero foams was taken before the solution passed through the foam. The PCA and CHG concentrations were taken using high performance liquid chromatography.

The solution was passed through the foam or felt material of each applicator to evaluate each of the five Libero foams (A-E) and the 3-1000Z felt separately. An aliquot was collected from each of the solutions after they were passed through each of the five foams and felt material. The PCA concentration each solution after it passed through each of the foams or felt material was obtained. The CHG concentration of each solution passed through the Libero foams was taken after the solution passed through the foam. The CHG concentration before and after the aqueous CHG solution with PCA was passed through the five Libero foams is shown below in Table 1.

TABLE 1

CHG concentration (% w/v) results obtained after passing an aqueous 2% CHG with 100-ppm PCA solution through Libero foams (A-E)

|   | Before Foam | After Foam | Reduction (%) |
|---|---|---|---|
| A | 2.05 | 2.04 | 0.5 |
| B | 2.05 | 2.04 | 0.5 |
| C | 2.05 | 1.97 | 3.9 |
| D | 2.05 | 1.94 | 5.4 |
| E | 2.05 | 2.06 | 0.5 |

Standard deviation ±5% may be expected due to variances in analytical conditions The PCA concentration before and after the aqueous CHG solution with PCA was passed through the five Libero foams and the 3-1000Z felt material is shown below in Table 2.

TABLE 2

PCA results obtained after passing an aqueous 2% CHG with 100-ppm
PCA solution through Libero foams (A-E) and 3-1000Z felt

|  | Before Foam | After Foam | Reduction (%) |
|---|---|---|---|
| A | 106 | 37 | 65 |
| B | 106 | 39 | 63 |
| C | 106 | 35 | 67 |
| D | 106 | 25 | 76 |
| E | 106 | 55 | 48 |
| 3-1000Z | 106 | 4 | >91 |

Standard deviation ±5% may be expected due to variances in analytical conditions Of the five Libero foams tested, the Libero foam "D" yield the best PCA reduction by decreasing the PCA concentration from 106 ppm to 25 ppm after the solution passed through the foam material. This represented a 76% reduction in PCA concentration. The "D" foam also reduced the concentration of CHG from 2.05% w/v to 1/94% w/v. This represented at 5.4% reduction in CHG concentration. The 3-1000z felt demonstrated a reduction in the PCA concentration from 106 ppm to less than 10 ppm. This represented a decreased PCA concentration greater that 91%. It was found that Libero foam "C" and "D" performed the best for use with aqueous CHG with respect to hydrophilicity, aqueous flow performance and absorbing PCA from the antiseptic.

EXAMPLE 2

A solution of one hundred (100) ppm PCA in a methanol/water matrix (50:50 v/v) solution without CHG was prepared. Twenty-six (26) ml the solution was added to six separate 26-ml applicators. Each applicator body was closed off by a different Libero foam or the 3-1000z felt material. The PCA concentration of each solution before it passed through the foam or felt material was obtained. The solution was passed through the foam or felt material of each applicator to evaluate each of the five Libero foams (A-E) and the 3-1000Z felt separately. An aliquot was collected from each of the solutions after they were passed through each of the five foams and felt material. The PCA concentration each solution after it passed through each of the foams or felt material was obtained.

The PCA concentration before and after the PCA solution was passed through the five Libero foams and the 3-1000Z felt material is shown below in Table 3.

TABLE 3

PCA results obtained after passing a 100-ppm PCA solution
through Libero foams (A-E) and 3-1000Z felt

|  | Before Foam | After Foam | Reduction (%) |
|---|---|---|---|
| A | 97 | 58 | 40 |
| B | 97 | 58 | 40 |
| C | 97 | 71 | 27 |
| D | 97 | 59 | 39 |
| E | 97 | 79 | 19 |
| 3-1000Z | 97 | 11 | 89 |

Standard deviation ±5% may be expected due to variances in analytical conditions Out of all the Libero foams tested, Libero foams A, B and D exhibited PCA reductions in the order of 39-40%. The PCA concentration decreased from its original 97 ppm before passing the solution through the foam material to 58 ppm for Libero foams A and B. Libero foam D resulted in a final PCA concentration of 59 ppm. The 3-1000Z felt decreased the PCA concentration from 97 ppm to 11 ppm. This represented an 89% reduction in PCA concentration.

EXAMPLE 3

One hundred (100) ppm of PCA was added to an aqueous 2% CHG solution. Twenty-six (26) ml the 100 ppm of aqueous CHG solution was added to three separate 26-ml applicators. Each applicator body was closed off by one of Libero felt 1.12, Libero felt 1.13 and 3-1000Z felt material. The PCA concentration of each solution before it passed through each felt was obtained. The CHG Concentration of each solution in the applicators closed off by Libero felts was taken before the solution passed through the foam.

The solution was passed through the felt of each applicator to evaluate each of the Libero felts and the 3-1000Z felt separately. An aliquot was collected from each of the solutions after they were passed through each of the felts. The PCA concentration each solution after it passed through the felt was obtained. The CHG concentration of each solution passed through the Libero felts was taken after the solution passed through the foam. The PCA and CHG concentration before and after the aqueous CHG solution with PCA was passed through the two Libero felts and the PCA concentration before and after the solution passed through the 3-1000Z felt is shown below in Table 4.

TABLE 4

CHG and PCA results obtained after passing aqueous 2% CHG
with 100 ppm PCA solution through Libero felts and 3-1000z felt

| | CHG Concentration (% w/v) | | | PCA Concentration (ppm) | | |
|---|---|---|---|---|---|---|
| | Before Felt | After Felt | Reduction % | Before Felt | After Felt | Reduction % |
| Felt 1.12 | 2.06 | 1.99 | 3.39 | 105 | 31 | 70 |
| Felt 1.13 | 2..06 | 1.96 | 4.85 | 105 | 11 | 90 |
| 3-1000Z | 2.06 | 2.06 | 0.00 | 105 | 8 | >90 |

Standard deviation ±5% may be expected due to variances in analytical conditions Two hundred (200) ppm of PCA was added to an aqueous 2% CHG solution. Twenty-six (26) ml the 200 ppm of aqueous CHG solution was added to three separate 26-ml applicators. Each applicator body was closed off by one of Libero felt 1.12, Libero felt 1.13 and 3-1000Z felt material. The PCA concentration of each solution before it passed through each felt was obtained. The CHG Concentration of each solution in the applicators closed off by Libero felts was taken before the solution passed through the foam.

The solution was passed through the felt of each applicator to evaluate the felts. As such, the solution was passed through each of the Libero felts and the 3-1000Z felt separately. An aliquot was collected from each of the solutions after they were passed through each of the felts. The PCA concentration each solution after it passed through the felt was obtained. The CHG concentration of each solution passed through the Libero felts was taken after the solution passed through the foam. The PCA and CHG concentration before and after the aqueous CHG solution with PCA was passed through the two Libero felts and the PCA concentration before and after the solution passed through the 3-1000Z felt is shown below in Table 5.

TABLE 5

CHG and PCA results obtained after passing aqueous 2% CHG with 200 ppm PCA solution through Libero felts and 3-1000z felt

|  | CHG Concentration (% w/v) | | | PCA Concentration (ppm) | | |
| --- | --- | --- | --- | --- | --- | --- |
|  | Before Felt | After Felt | Reduction % | Before Felt | After Felt | Reduction % |
| Felt 1.12 | 2.04 | 1.98 | 2.94 | 204 | 52 | 75 |
| Felt 1.13 | 2.04 | 1.96 | 2.45 | 204 | 34 | 83 |
| 3-1000Z | 2.04 | 2.06 | 0.98 | 204 | 15 | 93 |

Standard deviation ±5% may be expected due to variances in analytical conditions Three hundred (300) ppm of PCA was added to an aqueous 2% CHG solution. Twenty-six (26) ml the 300 ppm of aqueous CHG solution was added to three separate 26-ml applicators. Each applicator body was closed off by one of Libero felt 1.12, Libero felt 1.13 and 3-1000Z felt material. The PCA concentration of each solution before it passed through each felt was obtained. The CHG Concentration of each solution in the applicators closed off by Libero felts was taken before the solution passed through the foam.

The solution was passed through the felt of each applicator to evaluate the felts. As such, the solution was passed through each of the Libero felts and the 3-1000Z felt separately. An aliquot was collected from each of the solutions after they were passed through each of the felts. The PCA concentration each solution after it passed through the felt was obtained. The CHG concentration of each solution passed through the Libero felts was taken after the solution passed through the foam. The PCA and CHG concentration before and after the aqueous CHG solution with PCA was passed through the two Libero felts and the PCA concentration before and after the solution passed through the 3-1000Z felt is shown below in Table 6.

TABLE 6

CHG and PCA results obtained after passing aqueous 2% CHG with 300 ppm PCA solution through Libero felts and 3-1000z felt

|  | CHG Concentration (% w/v) | | | PCA Concentration (ppm) | | |
| --- | --- | --- | --- | --- | --- | --- |
|  | Before Felt | After Felt | Reduction % | Before Felt | After Felt | Reduction % |
| Felt 1.12 | 2.04 | 1.99 | 2.45 | 303 | 107 | 65 |
| Felt 1.13 | 2.04 | 2.01 | 1.47 | 303 | 66 | 78 |
| 3-1000Z | 2.04 | 1.07 | 1.47 | 303 | 41 | 86 |

Standard deviation ±5% may be expected due to variances in analytical conditions The Libero felt 1.12 demonstrated a reduction capacity to absorb PCA from the CHG solution in the range of 65-75%. The Libero felt 1.13 demonstrated a reduction capacity in the range of 78-90%. The 3-100Z felt demonstrated a reduction capacity in the range of 86 to higher than 90%.

EXAMPLE 4

Three different solutions containing 300, 200 and 100 ppm of PCA in a methanol/water matrix (50:50 v/v) were prepared. Twenty-six (26) ml the 300, 200 and 100 ppm of PCA solution were added to three separate 26-ml applicators, respectively. Each applicator body was closed off by one of Libero felt 1.12, Libero felt 1.13 and 3-1000Z felt material. The PCA concentration of each solution before it passed through each felt was obtained. The CHG Concentration of each solution in the applicators closed off by Libero felts was taken before the solution passed through the foam.

The solution was passed through the felt of each applicator to evaluate each of the Libero felts and the 3-1000Z felt separately. An aliquot was collected from each of the solutions after they were passed through each of the felts. The PCA concentration each solution after it passed through the felt was obtained. The PCA concentrations before and after the solution was passed through the two Libero felts and 3-1000Z felt are shown below in Table 7.

|  | 300 ppm solution | | | 200 ppm solution | | | 100 ppm solution | | |
| --- | --- | --- | --- | --- | --- | --- | --- | --- | --- |
|  | Before | After | % Red | Before | After | % Red | Before | After | % Red |
| Felt 1.12 | 296 | 119 | 60 | 195 | 99 | 49 | 99 | 62 | 37 |
| Felt 1.13 | 296 | 93 | 69 | 195 | 90 | 54 | 99 | 76 | 23 |
| 3-1000 Z | 296 | 76 | 74 | 195 | 58 | 70 | 99 | 30 | 70 |

Standard deviation ±5% may be expected due to variances in analytical conditions The Libero felt 1.12 demonstrated PCA percent reductions of 60, 49 and 37%, respectively, for solutions with 100, 200 and 300 ppm PCA containing no CHG. Libero felt 1.13 PCA percent reductions of 69, 54 and 23%. The 3-1000z felt demonstrated PCA reductions of 74, 70 and 70%.

Constructed and operated as previously described, an embodiment of the present invention provides an applicator and a method of reducing the concentration of unwanted by-products, such as PCA from aqueous CHG. More specifically, the present invention relates to a liquid applicator. The liquid applicator contains an antiseptic, such as aqueous CHG, and a porous element. In one embodiment, the porous element is a hydrophilic polyester-polyurethane foam material. As the antiseptic contacts the porous element the concentration of chemicals, such as PCA, are reduced in the antiseptic. The resulting filtered solution may be applied to the desired surface. The felts and foams described exhibit the ability to selectively, and reliably, absorb PCA from aqueous solutions containing CHG.

Operated as previously described, an embodiment of the present invention provides a method for reducing the concentration of unwanted chemicals in antiseptic, such as aqueous CHG. The antiseptic contacts a foam or felt material, such as polyurethane foam or felt, and the concentration of unwanted chemicals in the antiseptic is reduced. In one embodiment, the unwanted chemical in the antiseptic reduced is PCA.

From the foregoing, it will be seen that this invention is one well adapted to attain all the ends and objects hereinabove set forth together with other advantages which are obvious and which are inherent in the structure. It will be understood that certain features and subcombinations are of utility and may

Having thus described the invention, what is claimed is:

1. An applicator for applying an antiseptic solution to a desired surface and for selectively removing undesired by-products from the antiseptic solution, the applicator comprising:
   antiseptic solution in amount sufficient to be applied to a desired surface and to have an antimicrobial effect on the desired surface, the antiseptic solution comprising aqueous chlorhexidine gluconate; and
   at least one porous element, wherein the at least one porous element selectively removes undesired by-products from the antiseptic solution when the antiseptic solution contacts the at least one porous element.

2. The applicator of claim 1, wherein the undesired by-product is para-chloraniline.

3. The applicator of claim 2, wherein the at least one porous element is a hydrophilic polyester-polyurethane foam material.

4. The applicator of claim 3, wherein the hydrophilic polyester-polyurethane foam material has pore sizes from 70 to 130 per linear inch.

5. The applicator of claim 4, wherein the para-chloraniline in the antiseptic solution is reduced by 50-90%.

6. The applicator of claim 1, wherein the at least one porous element is a wetted applicator sponge.

7. The applicator of claim 1, wherein the antiseptic solution is contained in at least one ampoule and the antiseptic solution is released from the at least one ampoule and flows through the at least one porous element.

8. The applicator of claim 1, wherein the aqueous chlorhexidine gluconate is a solution in which water is the solvent in the largest concentration by volume.

9. An applicator for applying an antiseptic solution to a desired surface and for selectively removing undesired chemicals from the antiseptic solution, the applicator comprising:
   antiseptic solution in amount sufficient to be applied to a desired surface and to have an antimicrobial effect on the desired surface, the antiseptic solution being selected from the group consisting of aqueous chlorhexidine, alexidine, octenidine, alexidine, olanexidine and salts thereof;
   at least one porous element, wherein the at least one porous element selectively removes undesired chemicals from the antiseptic solution when the antiseptic solution contacts the at least one porous element.

10. The applicator of claim 9, wherein the antiseptic solution comprises alexidine dihydrochloride.

11. The applicator of claim 9, wherein the antiseptic solution comprises octenidine dihydrochloride.

12. The applicator of claim 9, wherein the antiseptic solution comprises olanexidine hydrochloride.

13. The applicator of claim 9, wherein the at least one porous element is a wetted applicator sponge.

14. The applicator of claim 9, wherein the antiseptic solution is contained in at least one ampoule.

15. The liquid applicator of claim 14 wherein the antiseptic solution is released from the at least one ampoule and flows through the at least one porous element.

16. A method for selectively removing unwanted by-products from a antiseptic solution, the method comprising;
   providing an antiseptic solution in amount sufficient to be applied to a desired surface and to have an antimicrobial effect on the desired surface, the antiseptic comprising aqueous chlorhexidine gluconate; and
   contacting the antiseptic solution with at least one porous element, wherein the at least one porous element selectively removes para-chloraniline from the antiseptic solution.

17. The method of claim 16, wherein the at least one porous element is a hydrophilic polyester-polyurethane foam material.

18. The method of claim 17, wherein the hydrophilic polyester-polyurethane foam material has pore sizes from 70 to 130 per linear inch.

19. The method of claim 18, wherein the para-chloraniline in the antiseptic solution is reduced by 50-90%.

20. The method of claim 16, wherein the chlorhexidine gluconate in the antiseptic solution is reduced no more than 5%.

* * * * *